(12) United States Patent  
Corwin et al.

(10) Patent No.: US 9,797,767 B2  
(45) Date of Patent: Oct. 24, 2017

(54) CALIBRATION OF MICROSCOPY SYSTEMS

(71) Applicant: GENERAL ELECTRIC COMPANY, Schenectady, NY (US)

(72) Inventors: Alex David Corwin, Niskayuna, NY (US); Christine Lynne Pitner, Niskayuna, NY (US); David Andrew Shoudy, Niskayuna, NY (US); Kevin Bernard Kenny, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 602 days.

(21) Appl. No.: 14/469,362

(22) Filed: Aug. 26, 2014

(65) Prior Publication Data

US 2016/0061654 A1 Mar. 3, 2016

(51) Int. Cl.
*G02B 21/36* (2006.01)
*G01J 1/02* (2006.01)
*G01N 21/64* (2006.01)
*G01N 21/27* (2006.01)

(52) U.S. Cl.
CPC .......... *G01J 1/0228* (2013.01); *G01N 21/274* (2013.01); *G01N 21/64* (2013.01); *G01N 21/6458* (2013.01); *G02B 21/365* (2013.01)

(58) Field of Classification Search
CPC ............... G06T 7/0012; G06T 7/80; G06T 2207/10056; G06T 2207/10144; G01J 1/0228; G01J 1/0295; G01J 2001/1673; G01N 21/274; G01N 21/64; G01N 21/6458; G02B 21/0076; G02B 21/365
See application file for complete search history.

(56) References Cited

U.S. PATENT DOCUMENTS

| | | | |
|---|---|---|---|
| 6,285,498 B1 | 9/2001 | Mayer | 359/392 |
| 7,698,000 B2 | 4/2010 | Silberberg et al. | 700/1 |
| 7,902,526 B2 | 3/2011 | Kim et al. | 250/492.2 |
| 8,390,682 B2 | 3/2013 | Minamide | 348/80 |
| 8,427,635 B2 | 4/2013 | Christiansen et al. | 356/243.1 |
| 8,563,913 B2 | 10/2013 | Dowski, Jr. et al. | 250/201.9 |
| 8,570,649 B2 | 10/2013 | Truong et al. | 359/385 |
| 2005/0270370 A1* | 12/2005 | Uemura et al. | 348/79 |
| 2007/0211243 A1* | 9/2007 | Laroche et al. | 356/243.1 |
| 2014/0226866 A1* | 8/2014 | Crandall et al. | G06T 7/0018 382/107 |
| 2015/0124072 A1* | 5/2015 | Wei et al. | H04N 17/002 348/79 |

FOREIGN PATENT DOCUMENTS

| | | | | |
|---|---|---|---|---|
| GB | 2447129 A | 9/2008 | | G02B 21/00 |
| WO | 2012096721 A1 | 7/2012 | | G01N 33/52 |
| WO | 2013049646 A1 | 4/2013 | | G02B 21/00 |

\* cited by examiner

*Primary Examiner* — Andrew W Johns
(74) *Attorney, Agent, or Firm* — Pabitra K. Chakrabarti

(57) ABSTRACT

Approaches are disclosed for calibrating a plurality of imaging devices, such as microscopes. In certain implementations, a calibration plate is employed that include a variety of calibration features. Imaging devices calibrated in accordance with the present approaches may be used to generate images having consistent attributes, such as brightness, regardless of which imaging device is employed.

14 Claims, 10 Drawing Sheets

| Serial # | 0104 | 0109 | 0105 | 0106 | 0111 |
|---|---|---|---|---|---|
| Master? | yes | no | no | no | no |
| ID | 5B31 | 5B31 | 5B31 | 5B31 | 5B31 |
| model | 2000 | 2000 | 2000 | 2000 | 2000 |
| Date | 2013-02-25 | 2013-02-25 | 2013-02-22 | 2013-03-12 | 2013-03-12 |
| Lamp Hours | 1852.40 | 1852.800049 | 1844.5 | 1883 | 1882.699951 |
| Script Version | 2/20/2013 | 2/20/2013 | 2/20/2013 | 3/5/2013 | 3/5/2013 |
| Operator | D.S. | D.S. | D.S. | D.S. | D.S. |
| Location | Storage | GRC | Syncro | GRC | Syncro |
| Holder Version | 2 | 1 | 1 | 2 | 2 |
| 2x_DAPI_CPS | 5506.22 | 5844.25 | 6126.88 | 5350.56 | 5122.017 |
| 2x_FITC_CPS | 38664.45 | 43443.28 | 42958.52 | 40580.08 | 38102.284 |
| 2x_CY3_CPS | 2704.31 | 3380.38 | 2650.22 | 2846.58 | 2633.819 |
| 2x_CY5_CPS | 100.31 | 113.00 | 104.62 | 102.31 | 93.844 |
| 10x_DAPI_CPS | 2990.17 | 3130.08 | 3260.79 | 3010.90 | 2848.172 |
| 10x_FITC_CPS | 4061.05 | 4654.02 | 4448.40 | 4497.07 | 4204.297 |
| 10x_CY3_CPS | 671.31 | 668.89 | 675.27 | 705.85 | 659.804 |
| 10x_CY5_CPS | 1560.07 | 1766.58 | 1612.86 | 1641.16 | 1498.010 |

FIG. 12A

| Serial # | 0104 | 0109 | 0105 | 0106 | 0111 |
|---|---|---|---|---|---|
| Master? | yes | no | no | no | no |
| ID | 5B31 | 5B31 | 5B31 | 5B31 | 5B31 |
| model | 2000 | 2000 | 2000 | 2000 | 2000 |
| Date | 2013-02-25 | 2013-02-25 | 2013-02-22 | 2013-03-12 | 2013-03-12 |
| Lamp Hours | 1852.40 | 1852.800049 | 1844.5 | 1883 | 1882.699951 |
| Script Version | 2/20/2013 | 2/20/2013 | 2/20/2013 | 3/5/2013 | 3/5/2013 |
| Operator | D.S. | D.S. | D.S. | D.S. | D.S. |
| Location | Storage | GRC | Syncro | GRC | Syncro |
| Holder Version | 2 | 1 | 1 | 2 | 2 |
| 20x_DAPI_CPS | 11679.01 | 12313.28 | 12796.41 | 12145.88 | 11408.615 |
| 20x_FITC_CPS | 5918.88 | 6582.09 | 5997.12 | 6507.39 | 5845.553 |
| 20x_CY3_CPS | 1165.38 | 1174.15 | 1146.91 | 1271.43 | 1173.313 |
| 20x_CY5_CPS | 2882.18 | 3402.08 | 3100.63 | 3119.06 | 2797.556 |
| 40x_DAPI_CPS | 665.24 | 615.80 | 655.25 | 743.53 | 602.210 |
| 40x_FITC_CPS | 1058.93 | 1027.70 | 898.67 | 1263.83 | 1132.720 |
| 40x_CY3_CPS | 394.28 | 351.78 | 337.35 | 422.43 | 407.926 |
| 40x_CY5_CPS | 911.65 | 1046.39 | 1003.39 | 944.58 | 880.114 |

FIG. 12B

CALIBRATION OF MICROSCOPY SYSTEMS

BACKGROUND

The subject matter disclosed herein relates to acquisition and analysis of images of biological samples. More particularly, the disclosed subject matter relates to the calibration of microscopes used in such image acquisition protocols.

Certain types of molecular pathology examinations utilize a multiplexing workflow for molecular pathology imaging. When generating images using such a multiplexing workflow, a single slice of tissue (i.e., a single sample) may be used. The multiplexing workflow allows images of the tissue sample acquired over multiple rounds of imaging to be layered, with each round of imaging being directed to a different set of biomarkers applied to the sample. Through the combination of biomarkers acquired over multiple rounds of imaging, a comprehensive view of tissue composition may be attained for the sample.

By way of example, in one such approach the tissue sample is repeatedly stained and bleached during a given imaging protocol. A round of image acquisition may be performed using an automated fluorescence microscope for background acquisition or after each stain or bleach cycle. For example, after an initial stain application a set of images may be acquired, after which the sample may be bleached and stained with the next biomarker and another set of images acquired. Multiple microscopes may be set up to process tissue samples in such a multiplexing workflow. However, in a conventional multiplexing workflow, all rounds of imaging for a given tissue sample are performed on a single microscope to eliminate variability that might otherwise be attributed to the differences in optical, geometric, and/or mechanical properties that may exist between different microscopes. By way of example, depending on the age and/or utilization of the lamps associated with each microscope in a fleet of microscopes, the brightness associated with each microscope may differ, leading to a lack of uniformity in terms of the illumination provided by each microscope.

With this in mind, one problem arising from such an approach for a given lab is how to load-balance a fleet of microscopes when, for example, one microscope is down for repair or is backed up with many tissue samples waiting for additional rounds of imaging while other microscopes sit idle. Among the problems that may exacerbate management of multiple microscopes in such an arrangement is the need to calibrate (e.g., optically, geometrically, mechanically, and so forth) all microscopes within a given lab relative to one another so that the layered images that are produced within a given lab are of high quality and are consistent over time, regardless of the microscope employed. Further, the calibration process should be as fast as possible to minimize downtime of the microscopes and to maximize the throughput (the number of tissue slides imaged per day) in the lab.

BRIEF DESCRIPTION

In one embodiment, a method is provided for determining a microscope exposure time. In accordance with this method a calibration plate is loaded onto a microscope stage such that the calibration plate is positioned in the object plane of the microscope. When the respective calibration plate is loaded, a calibration routine is executed that generates a set of calibration data for each objective and channel permutation of the microscope. For at least one objective and channel permutation, an intensity adjusted scale factor is calculated using the set of calibration data and a scale factor relating the respective calibration plate to a reference calibration plate or, if only a single respective calibration plate is employed, using a scale factor of 1. The intensity adjusted scale factors are used to determine an exposure time based on a photon count to be acquired at a given objective and channel combination.

In a further embodiment, a method is provided for performing an inter-plate calibration for a plurality of imager calibration plates. In accordance with this method, for each calibration plate of the plurality of calibration plates, a calibration routine is executed that generates a respective set of calibration data for each calibration plate. Each respective set of calibration data comprises measurements for each imager objective and channel permutation. A master calibration plate is designated from the plurality of calibration plates. The set of calibration data for the master calibration plate is the master calibration data. For each calibration plate, the respective set of calibration data for the respective calibration plate is divided by the master calibration data to calculate a set of scale factors for the respective calibration plate. Each scale factor corresponds to a different objective and channel combination.

In an additional embodiment, a method is provided for acquiring equivalent intensity images on different microscopes. In accordance with this method, an imaging protocol is received specifying one or more image acquisition parameters for imaging a sample provided on a stage of a calibrated microscope. The image acquisition parameters comprise at least an objective and channel. Based on the objective and channel, a photon count for image acquisition is determined for the calibrated microscope. An exposure time is derived based on the photon count and an intensity adjusted scale factor for the calibrated microscope. One or more images of the sample are acquired using the specified objective, channel, and exposure time.

In a further embodiment, a calibration plate is provided. The calibration plate includes two or more fluorescence reference slides. Each fluorescence reference slide fluoresces at one or more different target wavelengths.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 12A depicts a first portion of a table of inter-plate calibration data, in accordance with aspects of the present disclosure; and FIG. 12B depicts the second portion of the table of inter-plate calibration data started in FIG. 12A, in accordance with aspects of the present disclosure.

DETAILED DESCRIPTION

Figure 1:
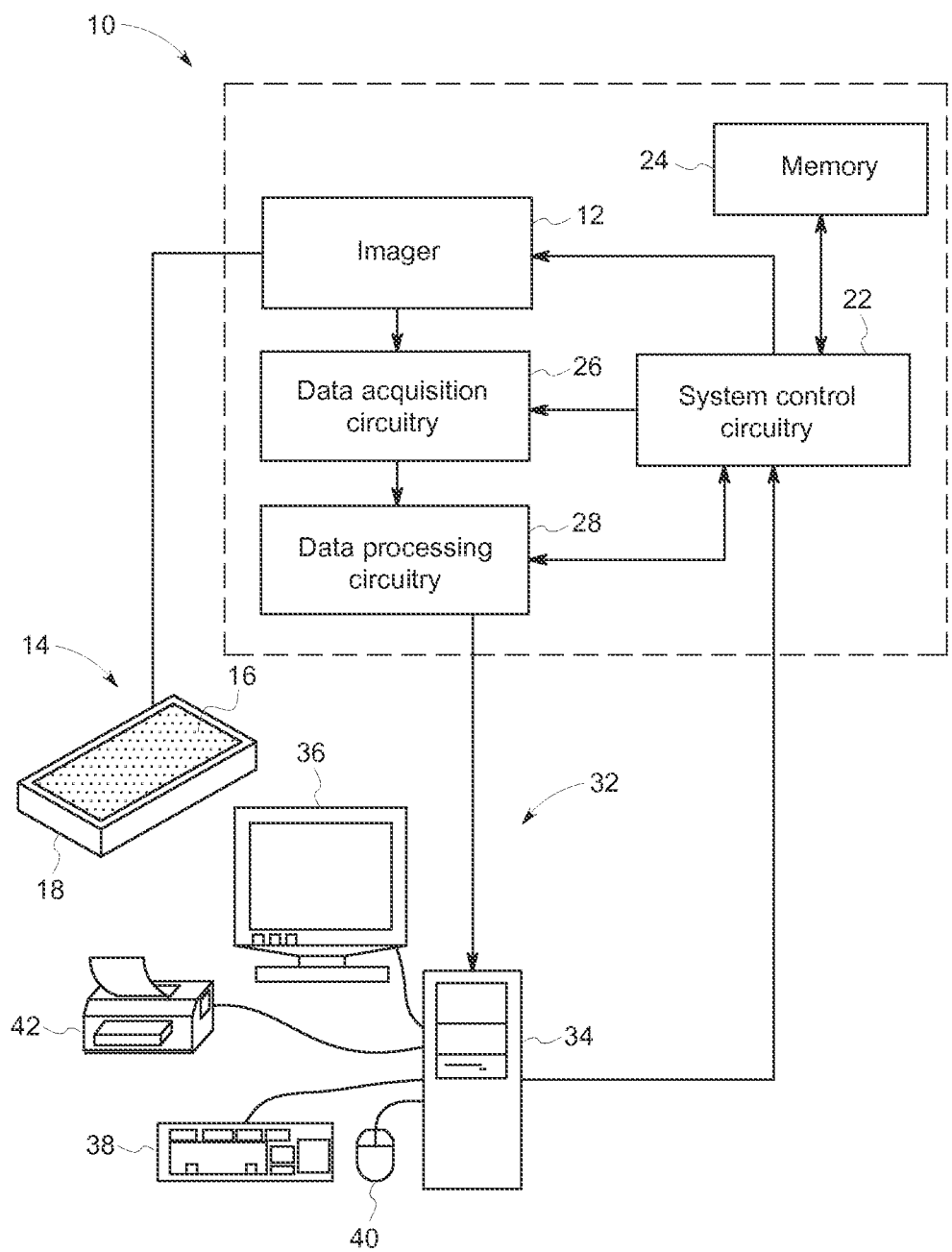
FIG. 1 is a diagrammatical view of an imaging system for use in acquiring image data of cells, in accordance with aspects of the present disclosure.

The present disclosure relates to a calibration device and associated methods for calibrating microscopes (e.g., fluorescent microscopes), such as with respect to intensity. In one embodiment, aspects of the approach employ a multi-slide calibration plate that is placed in the object plane of a microscope in the same position as where tissue samples are typically imaged. Alternatively, in other embodiments, the calibration plate may instead be built into (i.e., incorporated in the body of) the imager.

In one implementation, the calibration plate includes two or more solid fluorescent reference slides (which may each be partially covered by a neutral density filter) for measuring the intensity and shape of the illumination field for each combination of fluorescent channel (e.g., DAPI, FITC, CY3, CY5) and objective (e.g., 2×, 10×, 20×, 40×) in the system. Each fluorescent reference slide may correspond to one or more than one channel corresponding to a dye or wavelength of interest. In additional implementations, the calibration plate may be provided as a hybrid fluoro-chrome slide that further includes patterned features for performing geometry calibrations and/or a blank glass slide for measuring and removing artifacts due to background reflections.

By combining multiple calibration slides into a single plate, multiple (or all) calibration operations of the microscope can be fully automated, such as using processor-executable scripts or routines that operate the microscope with respect to the calibration plate. By placing the calibration plate directly in the object plane, the optical and/or geometric properties measured using the calibration plate are the same as the real properties that exist when imaging tissue samples, and therefore highly accurate calibrations can be attained.

Calibrations performed using the calibration plate with different microscopes ensure differences between the performance of different microscopes are minimized and that images acquired during different imaging rounds (such as in a multiplexed workflow) can be layered without introducing artifacts. Thus, by integrating the described calibration plates and methods into the workflow, the differences (e.g., intensity differences) between calibrated microscopes are reduced and load balancing can be performed to achieve higher throughput and lower turnaround time by utilizing available microscope resources. Further, by incorporating multiple (or all) desired calibration targets into a single plate and using fully automated calibration routines to measure and correct for the optical and geometric properties of each instrument, the calibration routines are able to be performed quickly and without user intervention. By way of example, as discussed herein, a calibration plate in accordance with the present disclosure may be used to establish a scanner-independent imaging protocol whereby each imager (e.g., microscope) is associated with a different exposure time to ensure equal illumination in terms of the total photons delivered to a specimen.

To provide consistency between calibrations, various technical implementations may be employed as aspects of the present approach. For example, the measured optical properties are strongly dependent on the focal plane. One challenge with using uniform fluorescent slides is the absence of a visible pattern for determining the quality of focus by conventional methods such as edge detection in the image. Therefore, in certain implementations laser focusing is used to excite a laser while sweeping the Z position of the objective and measuring the reflected laser signal. The observed reflected laser signal has a high value or measure as the focal plane moves through interfaces between material layers. An algorithm or other processor executable routine may be used to automatically select the first detected peak (which corresponds to the air to coverslip interface) or any other relevant detected peak corresponding to additional interfaces within the fluorescent slide stackup (e.g., coverslip to ND filter interface or ND filter to uniform fluorescent slide interface) to ensure consistent focusing during calibration.

With respect to intensity measurements and as discussed herein, it should be appreciated that a variety of mechanisms may be employed for determining the measured intensity during the calibration processes discussed herein. For example, in certain embodiments, measured intensity may be determined by computing a median image based on all or part of an imaged area. Similarly, in other embodiments, measured intensity may be computed based on the average intensity across all pixels (or a subset of pixels) from a median or non-median image. In other implementations, the measured intensity may be determined based on the average intensity at the center of illumination. Further, laser focusing may be employed to identify a first peak corresponding to the air-to-coverslip interface, thereby providing an identifiable and repeatable focusing plane which also yields a repeatable measured intensity during calibration on the uniform fluorescent calibration targets.

Further, in certain embodiments, to perform geometry-based calibrations in an automated manner, fast pattern matching algorithms may be used to find features of interest on the calibration plate (e.g., a hybrid fluoro-chrome slide as discussed herein). Such algorithms may be integrated in a closed-loop algorithm implementation and used to drive motion of the stage on which the calibration plate is positioned. Examples of such geometric calibrations include, but are not limited to: distortion calibration using idealized grid targets to an idealized distortion model, inter-microscope stage registration to an idealized master grid, and centration of objective coordinates within a given microscope, where all calibrations utilize laser focusing and pattern matching to guide the stage motions of multiple microscopes to the same patterned features.

In addition, as discussed herein, in certain implementations, multiple calibration plates may be created, each having slightly different optical and geometric properties. Therefore, in certain implementations, prior to using a calibration plate in the workflow for the first time, the optical scale factors and geometric offsets, scales, and rotations for a given plate are measured relative to a reference plate. By establishing and tracking the various properties of each calibration plate relative to such a reference plate (e.g., by knowing the correlation between plates as standardized based on the reference) accurate calibration of a group of microscopes may be maintained irrespective of which calibration plate is used to calibrate any given microscope. In practice, any calibration plate can serve as the reference plate for future integration of new plates as long as measurements are obtained for the other plates to be used with respect to the same reference plate.

With the preceding in mind, an example of an imaging system 10 capable of operating in accordance with the present approach is depicted in FIG. 1. Generally, the imaging system 10 includes an imager 12 (e.g., an automated fluorescence microscope) that detects signals and converts the signals to data that may be processed by downstream processors. As described more fully below, the imager 12 may operate in accordance with various physical principles, such as optical principles, for creating the image data. In general, the imager 12 generates image data, of any dimension, in a conventional medium, such as photographic film, or in a digital medium. For example, in some embodiments the imager 12 may generate substantially two-dimensional image data corresponding to an image acquired of a sample 14 provided on a slide in a staging area. In the depicted embodiment, the imager 12 is configured to image sample 14 in the form of a tissue sample 16 (such as one or more layers of cells or tissue suitable for molecular pathology) provided on a slide 18 or other suitable imaging substrate.

In certain embodiments, the imager 12 may provide different degree of magnification. For example, in one implementation, the imager 12 may be a microscope, such as a high-throughput microscope, suitable for image and/or video acquisition using magnification and at suitable light wavelengths (such as visible, infrared, and/or ultraviolet light wavelengths). Thus, the imager 12 may be a fluorescence microscope, a confocal fluorescence microscope, a laser scanning confocal microscope, a total internal reflection fluorescence microscope, or any other suitable microscopy device.

In one embodiment, the imager 12 operates under the control of system control circuitry 22. The system control circuitry 22 may include a wide range of circuits, such as circuitry controlling the emission of various types of electromagnetic radiation (such as visible, infrared, and/or ultraviolet light, or other electromagnetic wavelengths suitable for imaging) for use in the imaging process. Likewise, in some embodiments, the system control circuitry 22 may include timing circuitry, circuitry for coordinating data acquisition in conjunction with movement of a sample and/or the imager optics, circuitry for controlling the position of the imager 12 and/or the samples 14 undergoing imaging, and so forth.

In the present context, the imaging system 10 may also include memory elements 24, such as magnetic, solid state, or optical storage media, for storing programs and routines executed by one or more general or special purpose processor components, which may be provided as part of the system control circuitry 22 and/or as part of other components of the system 10, such as data acquisition circuitry 26 and/or data processing circuitry 28. The stored programs or routines may include programs or routines for performing aspects of the presently disclosed approach.

In the depicted embodiment, data acquisition circuitry 26 is employed to acquire image data from the imager 12. In optical embodiments, the data acquisition circuitry 26 may be configured to acquire image data via one or more optical sensing elements, including digital imaging circuitry. The acquired image data may in certain embodiments, represent images of the sample 14 acquired at a given magnification and for a given biomarker. In embodiments where the initially acquired image data is analog in nature, the data acquisition circuitry 26 may also be configured to convert the analog data to a digital format. Likewise, the data acquisition circuitry 26 may be configured to provide some initial processing of the acquired image data, such as adjustment of digital dynamic ranges, smoothing or sharpening of data, as well as compiling of data streams and files, where desired.

The image data acquired by the data acquisition circuitry 26 may be processed, such as by data processing circuitry 28 in the depicted embodiment. For example, in certain embodiments, the data processing circuitry 28 may perform various transformations or analyses of the image data, such as ordering, segmenting, sharpening, smoothing, feature recognition, and so forth. Prior or subsequent to processing, the image data may be stored, such as in memory elements 24 or a remote device, such as a picture archiving communication systems or workstation connected to the imaging system 10, such as via a wired or wireless network connection. In multiplexed workflows, as described herein, multiple images may be acquired of a tissue sample 16, where different images are acquired after treatment of the tissue sample 16 with different biomarkers or stains.

The raw or processed image data may, in some embodiments, be provided to or displayed on an operator workstation 32. In multiplexed embodiments, as discussed herein, multiple images of a tissue sample 16 acquired using different biomarkers or stains may be visually layered to allow review of a stack or set of images of the tissue sample 16 at one time on the operator workstation. In addition, the operator workstation 32 may be configured to control and/or monitor the above-described operations and functions of the imaging system 10, such as via an interface with the system control circuitry 22.

The operator workstation 32 may be provided as a general purpose or application specific computer 34. In addition to a processor, the computer 34 may also include various memory and/or storage components including magnetic and optical mass storage devices, internal memory, such as RAM chips. The memory and/or storage components may be used for storing programs and routines for performing operations described herein that are executed by the computer 34 or by associated components of the imaging system 10. Alternatively, the programs and routines may be stored on a computer accessible storage and/or memory remote from the computer 34 but accessible by network and/or communication interfaces present on the compute 34.

The computer 34 of the operator workstation 32 may also comprise various input/output (I/O) interfaces, as well as various network or communication interfaces. The various I/O interfaces may allow communication with user interface devices of the operator workstation 32, such as a display 36, keyboard 38, mouse 40, and/or printer 42, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

Though a single operator workstation 32 is depicted for simplicity, the imaging system 10 may actually be in communication with more than one such operator workstation 32. For example, an imaging scanner or station may include an operator workstation 32 used for regulating the parameters involved in the image data acquisition procedure, whereas a different operator workstation 32 may be provided for viewing and evaluating results, i.e., a stack or layered presentation of pathology images generated for a tissue sample 16.

For the purpose of explanation, certain functions and aspects of the present technique have been described as being separate and distinct or as being associated with certain structures or circuitry. However, such distinctions have been made strictly to simplify explanation and should not be viewed as limiting. For example, for simplicity the preceding discussion describes implementation via a discrete imaging system 10 and operator workstation 32. As will be appreciated, however, certain functions described as being performed by the imaging system 10, such as data acquisition, data processing, system control, and so forth, may instead be performed on the operator workstation 32 or may have differing aspects, some of which are performed on the imaging system 10 and others of which are performed on the operator workstation 32. Indeed, in practice, virtually all functions attributed to the imaging system 10, with the possible exception of the functions attributed to the imager 12, may be performed on an operator workstation 32. In other words, the data acquisition circuitry 26, memory 24, data processing circuitry 28, and/or system control circuitry 22 may be provided as hardware or firmware provided in an operator workstation 32 and/or as software executable by the operator workstation 32. For example, some or all of the circuitry described herein may be provided as routines executed on a suitable processor or coprocessor of a computer 34 of an operator workstation 32. Indeed, it should be understood that the term circuitry, as used herein, encompasses, dedicated or generalized hardware or firmware implementations and/or processor-executable software implementations suitable for implementing the described functionality.

With the preceding in mind, calibration of an imager 12 (or group of imagers 12) may be accomplished using the methodology and calibration plates discussed herein. In one embodiment the calibration plate combines multiple calibration targets (e.g., multiple uniform fluorescent slides, patterned features, and/or blank glass) onto a single surface or substrate, which is distinct from prior approaches and which allows multiple optical and geometric properties of the imager 12 to be calibrated using a single calibration plate. In one embodiment, the presently disclosed calibration plate is loaded into the imager 12 (e.g., a fluorescence microscope) in the same manner as a slide or other sample which would typically be imaged by the imager. That is, the calibration plate is inserted directly into the object plane. In other embodiments, the calibration plate may be built in to the imager 12.

A calibration protocol may then be executed, such as by an automated calibration routine, to obtain data using the calibration plate that may be used to compensate for camera rotation, objective XYZ offsets, objective scaling, XY stage scale factors, XY stage rotation, distortion calibration, background reflections, flattening of the illumination field, and intensity and absolute stage position differences (i.e., stage registration) between imagers (e.g., microscopes). In one embodiment, the geometry calibrations are performed for each objective (e.g., 2×, 10×, 20×, 40×) and the optical calibrations are performed for each combination of objective and channel, where the channels typically correspond to a specific fluorescence or biomarker band (e.g., DAPI, FITC, CY3, CY5).

Figure 2:
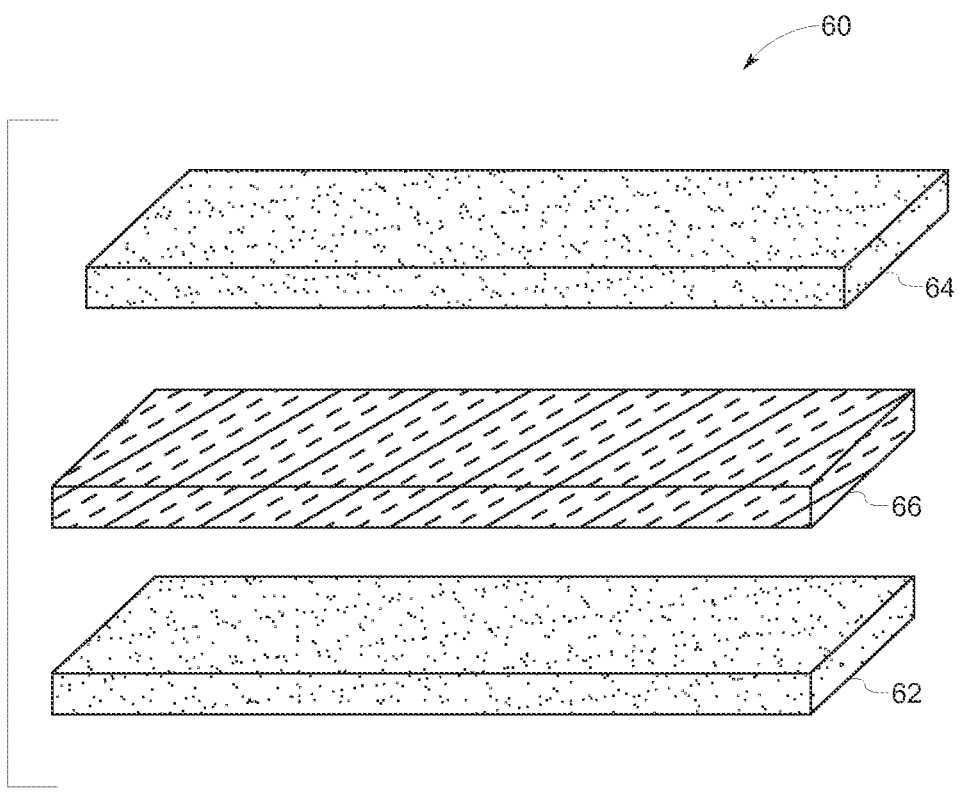
FIG. 2 depicts a laminate structure, in accordance with aspects of the present disclosure.

With the preceding in mind, an example of one embodiment for constructing a calibration plate as used herein is provided. Turning to FIG. 2, in this example, a laminate 60 (i.e., a structure of multiple layers of material) is formed by laminating (i.e., stacking multiple layers of material using adhesive without introducing bubbles) three layers 62, 64, 66 together to create a 100 µm thick stack structure. The lamination process may be performed using a suitable vacuum laminator machine. In one implementation, the three materials laminated to form the laminate stack 60 are a 50 µm thick layer 62 of adhesive (e.g., ARclear 8932EE from Adhesives Research), a 25 µm thick layer 64 of adhesive (e.g., EL-8026 from Adhesives Research), and a 25 µm thick layer 66 of a polyimide film (e.g., Kapton® or Kapton® HN from Dupont).

In one embodiment, prior to lamination the polyimide film layer 66 undergoes a reactive ion etch (RIE) process. In other embodiments, the RIE etch step may be omitted. When performed, the reactive ion etch process roughens the surface of the polyimide film layer 66 on a microscale, which helps increase the bond strength between the polyimide film and the adhesive. By way of example, a RIE process may be employed in which the $O_2$ flow is 75 sccm, pressure is 50 mTorr, and power is 300W and where a quartz cover plate is employed. Duration of the RIE in such an example may be 10 minutes for a single frame or 12 minutes for two frames.

Separate from the process of preparing the laminate stack 60, a set of fluorescence reference slides are prepared, such as by cutting or otherwise forming an existing set of reference slides to a specified size or shape. For example a set of fluorescence reference slides may be obtained, such as a blue fluorescence reference slide suitable for transmitting wavelengths at approximately 425 nm to 450 nm (suitable for imaging DAPI, Indo, and Fura), a green fluorescence reference slide suitable for transmitting wavelengths at approximately 500 nm to 575 nm (suitable for imaging FITC and GFP), and a red fluorescence reference slide suitable for transmitting wavelengths at approximately 600 nm to 675 nm (suitable for imaging Rhodamine and Texas Red). In other embodiments, more or less than three fluorescence reference slides may be employed. Further, in some embodiments, a given fluorescence slide may be used for calibrating more than one fluorescent channel (i.e., wavelength). For example, a blue reference slide as described herein may be suitable for calibrating fluorescent channel for use with DAPI dye and another fluorescent channel for use with CY5 dye. In one embodiment, each larger fluorescence reference slide may be cut or scored and broken to rectangular shapes having dimensions of approximately 5.1 cm (i.e., 2 inches) by 2.4 cm (i.e., approximately 1 inch).

In one implementation, in addition to preparing the laminate stack 60 and fluorescence reference slides, a set of neutral density filters are prepared. For example three densities of neutral density filters (e.g., ND 0.5, ND 1, and ND 2) may be prepared for inclusion on the calibration plate. In one embodiment, one each of the ND 0.5 and ND 2 neutral density filter are prepared and two of the ND 1 filter are prepared. In one embodiment, the starting materials for preparing the neutral density filters may be respective Kodak Wratten 2 Neutral density filters that are 3" square and are 0.5, 1, and 2 OD, such as NT54-455, NT53-705, and NT53-706 obtainable from Edmund Optics. The neutral density filters may be cut to the desired size using a plotter executing a dxf or gsd file encoding appropriate instructions.

Figure 3:
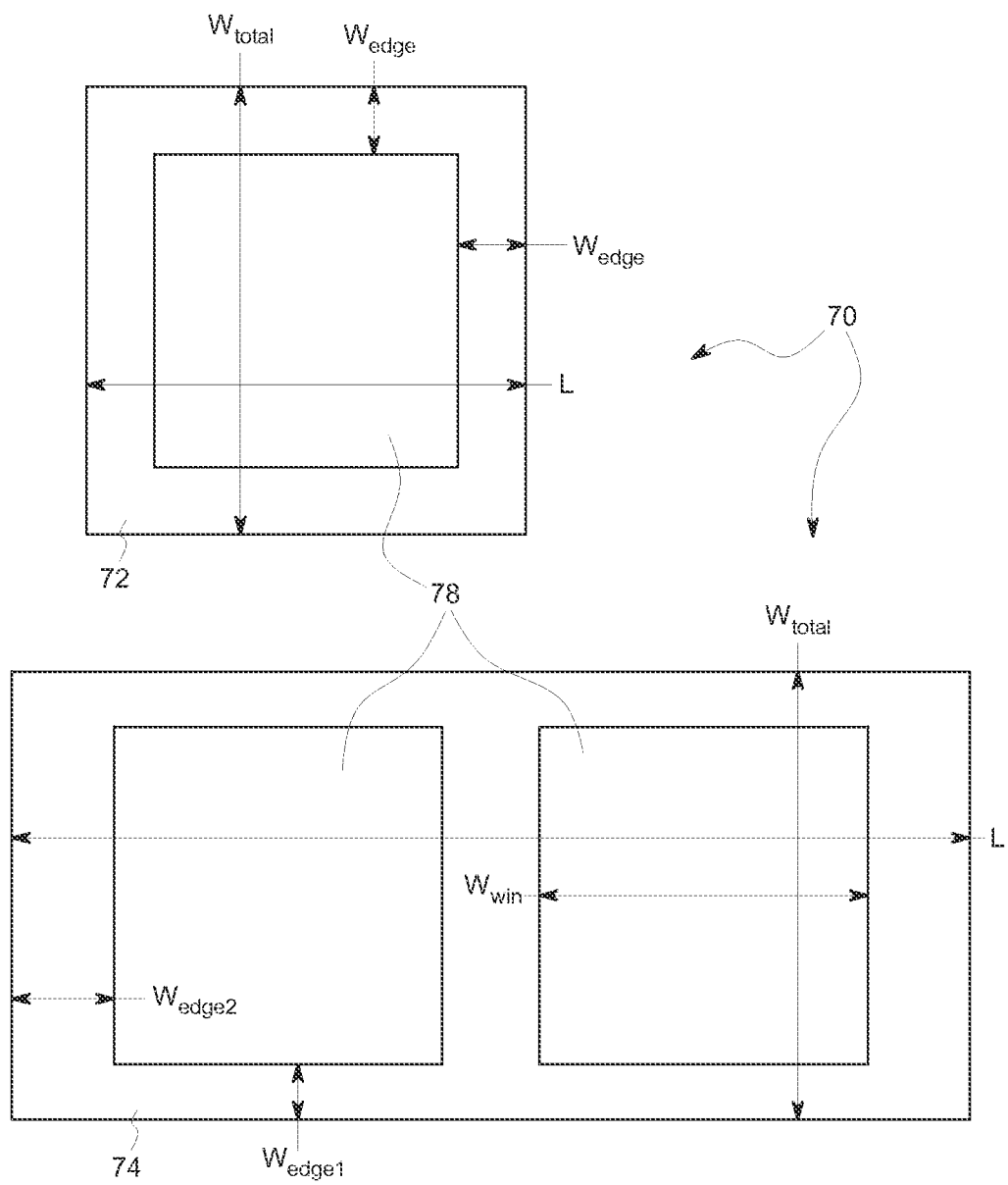
FIG. 3 depicts adhesive frames, in accordance with aspects of the present disclosure.
Figure 4:
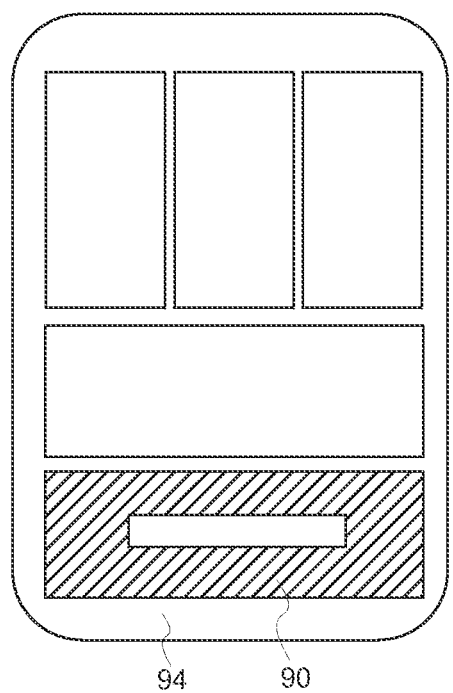
FIG. 4 depicts a calibration plate after addition of a chrome-on-glass slide, in accordance with aspects of the present disclosure.

With the preceding in mind, in one embodiment the laminate stack 60 is used to form adhesive frames for holding the respective fluorescence reference slides and neutral density filters. In one implementation, two types of adhesive frames may be formed: single frames and double frames. The adhesive frames may be formed using a platter to cut the laminate material into the desired frame shapes. Examples of suitable adhesive frames 70 are depicted in FIG. 3, where a square single adhesive frame 72 is depicted which has a length and width of 24 mm and where the edge of the frame is 3.556 mm across. Similarly, a double frame 74 is depicted which is rectangular, having an overall length of 50 mm and width of 24 mm, edges in the width-wise direction that are 3.556 mm, edges in the length-wise direction that are 5 mm, and windows 78 within the double frame 74 which are square and 16.88 mm across.

With the foregoing preparations completed, a calibration plate for use in accordance with the present disclosure may be assembled. Turning to FIGS. 4-8 (showing a bottom view of the calibration plate 94 during assembly), in one implementation a chrome-on-glass slide 90 (such as a model IAM-8-P-CG slide obtainable from Applied Image Inc.) may be affixed at a first position (such as using adhesive strips) to a calibration plate 94, chrome-side down such that the gold-surface of the chrome-on-glass slide remains facing the user and the text or patterns on the chrome-on-glass slide are visible and legible. In one embodiment, a blue fluorescence reference slide is positioned between the chrome surface of the chrome-on-glass slide 90 and the calibration plate 94.

Figure 5:
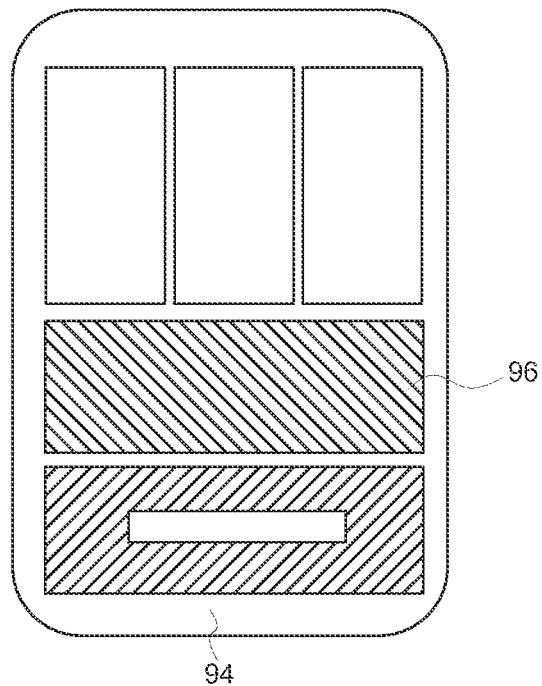
FIG. 5 depicts a calibration plate after addition of an unfrosted glass slide, in accordance with aspects of the present disclosure.
Figure 8:
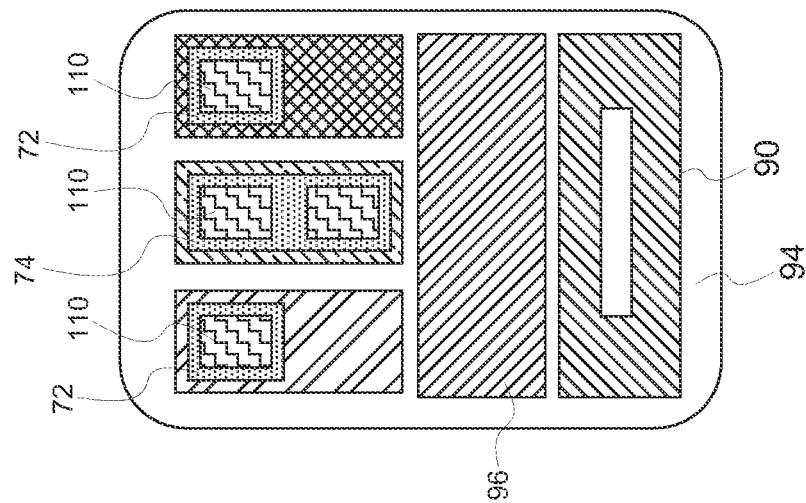
FIG. 8 depicts a calibration plate after addition of neutral density filters, in accordance with aspects of the present disclosure.

In one embodiment, at a second position on the calibration plate 94 a glass slide 96, such as an unfrosted, 24 mm×50 mm glass slide, may be affixed, such as by adhesive strips. Such a step is illustrated in FIG. 5 in which a glass slide 96 is shown affixed to the bottom of the calibration plate 94 at a second position relative to the chrome-on-glass slide 90.

Figure 7:
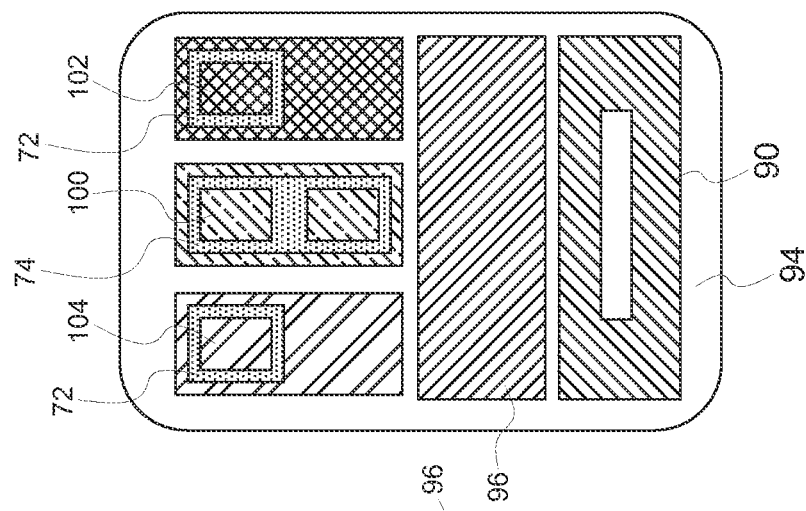
FIG. 7 depicts a calibration plate after addition of adhesive frames, in accordance with aspects of the present disclosure.
Figure 6:
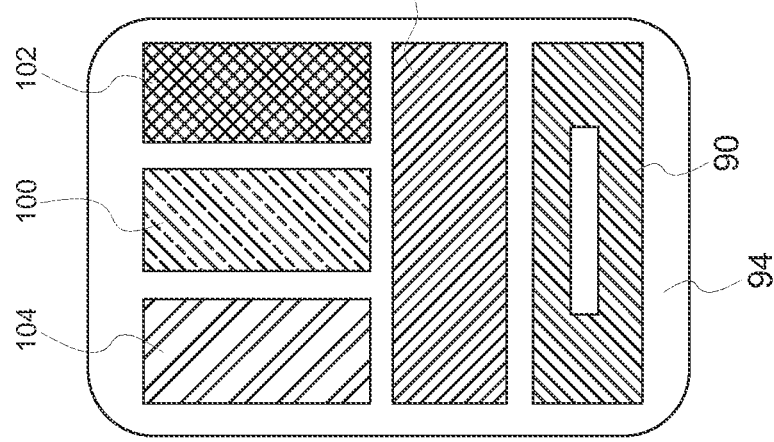
FIG. 6 depicts a calibration plate after addition of fluorescence reference slides, in accordance with aspects of the present disclosure.
Figure 9:
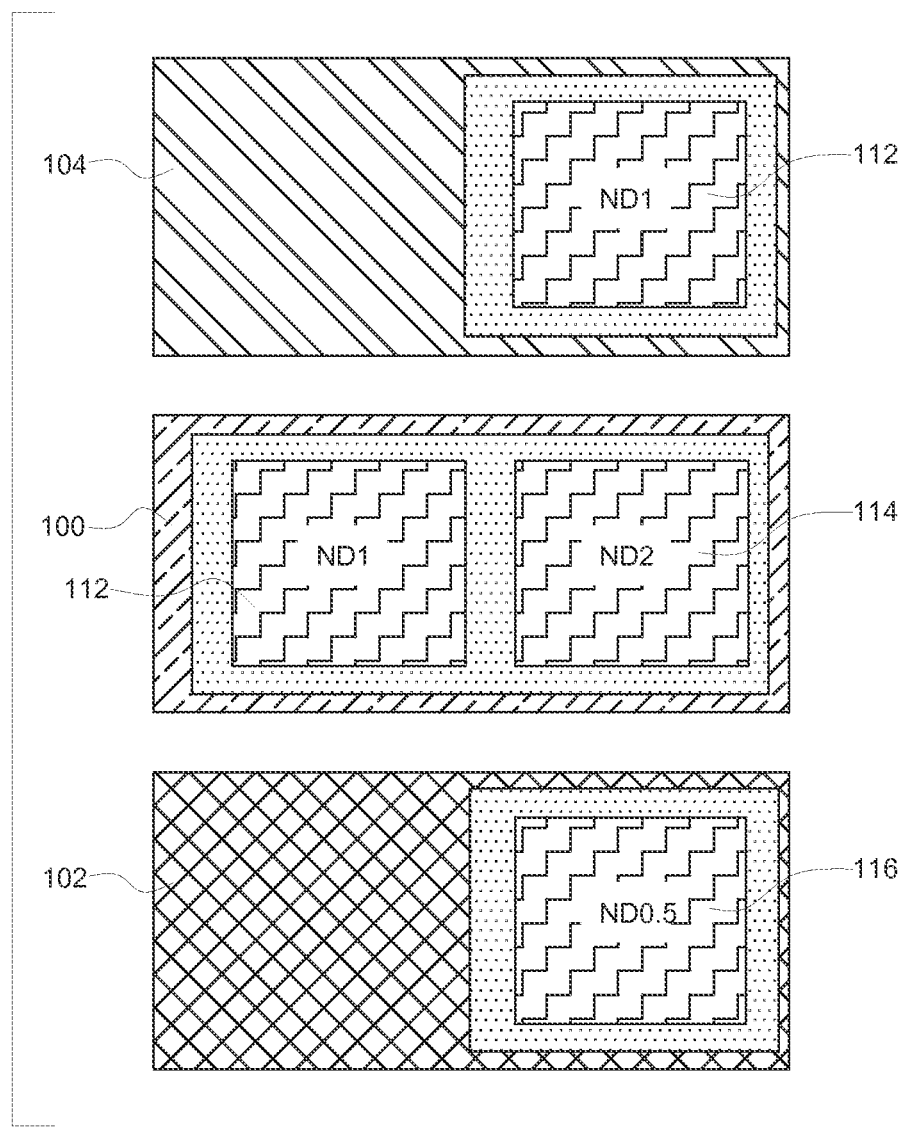
FIG. 9 depicts a further detail of the fluorescence reference slides, adhesive frames, and neutral density filters, in accordance with aspects of the present disclosure.

Turning to FIG. 6, in the depicted example, three fluorescence reference slides which fluoresce at different characteristic wavelengths (e.g., a red fluorescence reference slide 100, a blue fluorescence reference slide 102, and a green fluorescence reference slide 104) are affixed to the calibration plate 94 at respective third, fourth, and fifth positions. Turning to FIG. 7, once the fluorescence reference slides are in place, the adhesive frames 70 (e.g., single adhesive frames 72 and double adhesive frame 74) are applied to the fluorescence reference slides. In the depicted example, and turning to FIG. 8, a set of neutral density filters 110 are applied to the adhesive frames 72, 74 with respect to the fluorescence reference slides. In this example, a 0.5 neutral density filter 116 is applied to the blue fluorescence reference slide 102, a 1.0 neutral density filter 112 is applied to the green fluorescence reference slide 104, and 1.0 and 2.0 neutral density filters 112, 114 are applied to the red fluorescence reference slide 100 (using a double frame 74). Subsequent to the placement of the neutral density filters, a coverslip (e.g., a 24 mm×24 mm coverslip) may be adhered to the edges of the adhesive frames 72, 74 over each neutral density filter.

A calibration plate 94 as discussed herein may be used for a variety of different calibration operations. For example, the calibration plate embodiment discussed above may be used for automated calibrations that include, but are not limited to, the following. (1) Camera rotation calibration—may use a patterned feature on the hybrid fluoro-chrome slide 90 to determine the relative rotation (in degrees) between the camera and X-axis motion stage. When scanning an area of tissue bigger than a single field of view (FOV) and then piecing the resulting set of images together (stitching), it is useful to know the rotation of the images relative to the X stage for accurate stitching with minimal visible artifacts. (2) Objective centration calibration—may use a patterned feature on the hybrid fluoro-chrome slide 90 to determine the XY offset between objectives within the microscope system (i.e. 2×, 10×, 20×, 40×, etc.) so that when switching objectives and applying the offset correction factors, a given feature of interest remains in the center of the FOV. (3) Objective z-focus—may use a patterned feature on the hybrid fluoro-chrome slide 90 to determine the Z offset between objectives within the microscope system for obtaining optimal focus so that when switching objectives and applying the offset correction, the image remains in focus. (4) Objective scale factors—may use a patterned feature on the hybrid fluoro-chrome slide 90 to determine the exact magnification of each objective. This may be used by registration algorithms and during acquisition to determine how far to move the XY stage when imaging a region comprising multiple FOVs. (5) Stage motion scale factors—may use a patterned feature on the hybrid fluoro-chrome slide 90 to determine how far the XY stages will move relative to a commanded distance in [mm/pix] units. By knowing the X and Y stage scale factors, the move operations can be performed accurately during acquisition. (6) Stage rotation—may use a patterned feature on the hybrid fluoro-chrome slide 90 to determine the rotation of the Y stage, where the X stage is used as the reference (0 degrees of rotation). By knowing this rotation, accurate move operations can be performed during acquisition. (7) Absolute stage position—may use a patterned feature on the hybrid fluoro-chrome slide 90 to determine the absolute position of this feature. An XY offset is computed that is normalized to the reference calibration plate and this offset is applied during all subsequent rounds of acquisition to create a common coordinate system across multiple microscopes, such that for a common slide, a move command to (X,Y) on any microscope will center the same feature in the FOV. (8) Background compensation—may use the blank glass slide 96 to determine a median reflection pattern for each objective/channel combination. A scaled version of the median reflection pattern image (scaled based on exposure time) is subtracted from subsequent images during acquisition. (9) Field flattening compensation—may use uniform fluorescent slides 100, 102, 104 to determine the shape of the illumination profile for each objective/channel combination. The shape is characterized by a set of coefficients, and the inverse of these coefficients are used to flatten the illumination field of acquired images such that there is uniform intensity throughout the entire FOV. (10) Intensity calibration—may use the uniform fluorescent slides 100, 102, 104 to determine the average intensity of each objective/channel combination in [counts/second] units so that exposure times can be scaled during acquisition to achieve consistent image intensity between multiple microscopes. (11) Distortion compensation or correction—may use a geometric grid pattern on the hybrid fluoro-chrome slide 90 to characterize distortion throughout the entire FOV for each objective/channel combination. The distortion is characterized by a set of coefficients that are saved and later used to de-distort the acquired images, which reduces ghosting and blurring at the intersections between adjacent FOVs when producing stitched images in the registration algorithms. Distortion calibration may use geometric grid targets which are registered to an idealized distortion model.

With the preceding examples of a suitable embodiment of a calibration plate 94 (and its construction) and suitable calibration uses in mind, an example of the use of such a calibration plate 94 is discussed in greater detail below. In particular, in one embodiment a calibration plate 94 such as described in the preceding examples may be used to implement a scanner independent imaging protocol to automatically provide for one or more of the calibration operations set forth above. For example, one such protocol may utilize a calibration plate 94 to derive individual exposure times for each imager 12 (e.g., microscope) in a lab or other analysis group such that equal illumination is obtained on each imager 12 in terms of the total photons to which each sample is exposed. That is, in one such imaging protocol, per microscope exposure times may be generated such that brightness differences between microscopes are accounted for to ensure equal illumination (in terms of total photons emitted) of specimens, regardless of which machine is employed.

In accordance with one such approach the calibration information is used to set the exposure time during image acquisition, allowing images to be acquired with uniform photon exposure. This is in contrast to approaches in which the calibration information is instead passed down-stream for post acquisition processing and adjustment. In this manner, images may be acquired with substantially the same number of photons per exposure event such that signal-to-noise values of identical samples taken on different imagers 12 will be substantially equal. As will be appreciated, some differences may exist due to longer exposure times being penalized due to dark current, however for cooled detectors such differences will be below the Poisson square root of the N noise floor and, thus, negligible.

Figure 10:
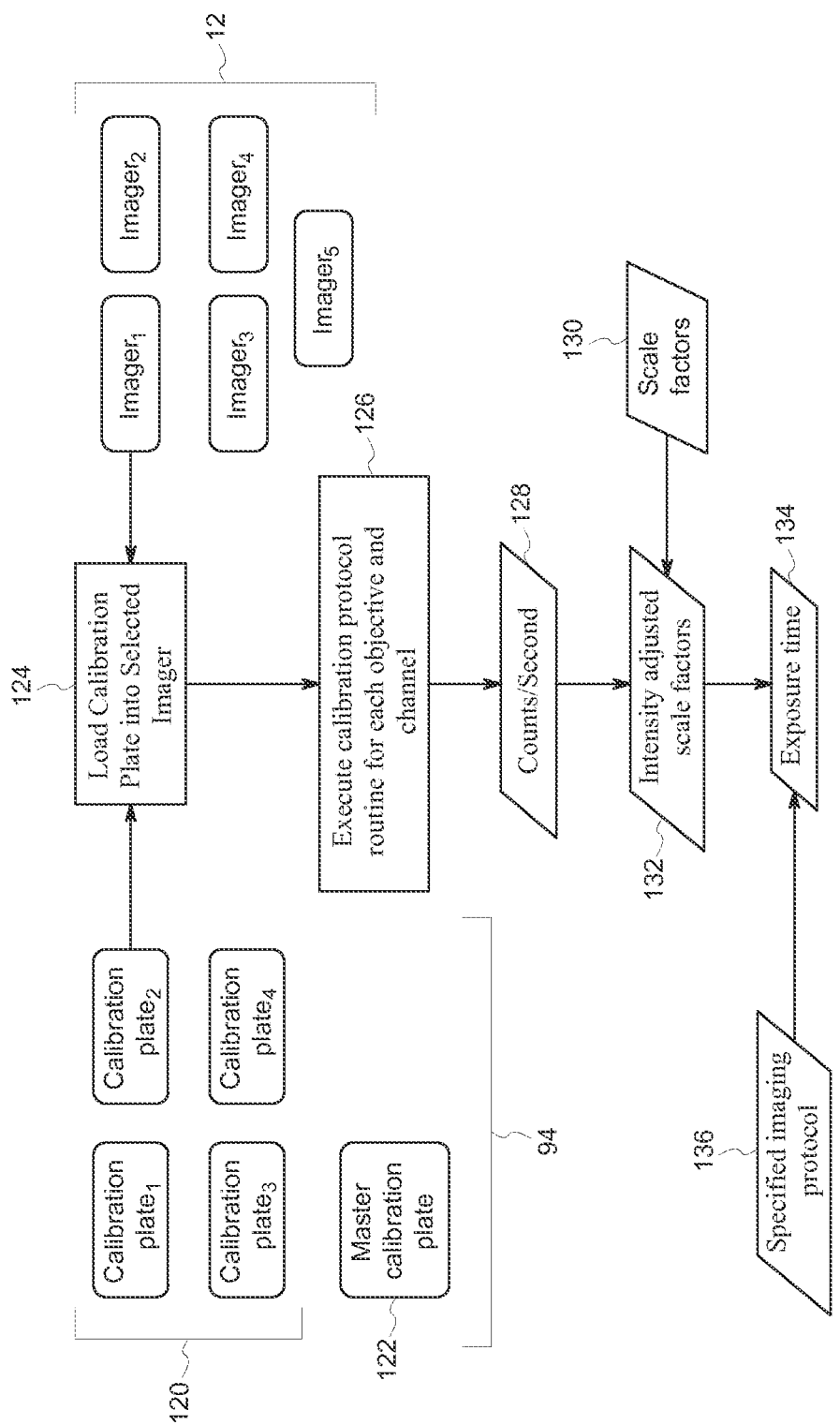
FIG. 10 depicts a process flow diagram demonstrating calibration and use of an imager, in accordance with aspects of the present disclosure.

With this in mind, and turning to FIG. 10, in one implementation calibration values are periodically (e.g., weekly, monthly, and so forth) determined (using a calibration plate 94, as described above) for each objective and channel (e.g., color or biomarker channels) of each imager 12 (e.g., microscope) which is to be calibrated relative to one another. In one example, as depicted in FIG. 10, a master calibration plate 122 (i.e., a reference plate) may be used to standardize a set of non-master calibration plates 120, any one of which may be used to calibrate one of a set of imagers 12 (which may be in the same or different locations). In the depicted example, one of a set of calibration plates is loaded (block 124) into an imager 12. Once loaded, a calibration routine or protocol may be executed (block 126), such as by a controller of the imager 12.

As used herein, the calibration information obtained for each objective and channel combination of a given imager 12 (e.g., microscope) may include $I_{cal}$, the photon counts per second 128, which may be used to calculate a scale factor, S, 130 for a given non-master calibration plate 120 with respect to the master calibration plate 122, as discussed in greater detail below. That is, for each given channel and objective combination, a scale factor S may be determined that relates the values obtained for a given calibration plate 120 to those obtained for the master calibration plate 122. For example, in one embodiment, the scale factor S is defined as the ratio of the $I_{cal}$ for a particular magnification and channel of the current calibration plate 120 being used in a calibration procedure relative to the corresponding $I_{cal}$ values which would be obtained using the reference or master calibration plate 122 at that magnification and channel on the imager 12 in question. Thus, when S is >1, the current calibration plate will give more counts per second (CPS) (i.e., a brighter image) than is seen using the reference or master calibration plate 122 for the imager 12 in question. Where no master calibration plate is employed, or where a single calibration plate is present, a scale factor of 1 may be employed.

Once a scale factor 130 is known for a given imager 12, objective, and channel, this information may be used to generate images using the imager 12 that have equivalent brightness to those generated by other imagers 12 calibrated to the same master calibration plate 122. As depicted in FIG. 10, blocks 130-136 disclose these aspects of the disclosure. In this example of an implementation, exposure counts ($C_{exp}$) are employed instead of time measurements. That is, counts are the relevant unit of measurement. The counts, in this example, are equated to the number of photons incident on the surface being imaged on a calibration plate 94.

As will be appreciated, in practice the count may be an indirect measure of the number of incident photons. In particular, in certain practical embodiments, a count value may be determined from an output of an analog-to-digital converter that measures voltage in a CMOS well and this voltage is proportional to the number of electrons ejected from a set of photon events. That is, electrons per photon at a given wavelength and well capacitance may both be specified, with the measured voltage being used as a surrogate for the count measure of interest.

With the preceding in mind, to convert an exposure time on a particular objective/channel combination to counts, the following calculation is performed:

$$C_{exp} = \frac{tI_{cal}}{S} \quad (1)$$

where t is time in units of seconds. Inversely, the conversion from an exposure count to an exposure time 134 (in seconds) is given by:

$$t = \frac{SC_{exp}}{I_{cal}}. \quad (2)$$

For simplicity, an effective intensity adjusted scale factor, $S_{cal}$, 132 for a given calibration plate can be defined for each objective/channel combination such that:

$$S_{cal} = \frac{S}{I_{cal}}. \quad (3)$$

The equation for exposure time 134 in terms of exposure counts for a specified protocol 136 can, therefore, may be expressed as:

$$t = S_{cal} C_{exp}. \quad (4)$$

With the preceding discussion in mind, the following example is provided to further describe aspects of the present calibration approach. For a given imager 12 (e.g., microscope) and calibration plate 94, the scale factor S (130), photon counts per second $I_{cal}$ 128), and intensity adjusted scale factor $S_{cal}$ (312), can be determined for each combination of objective (i.e., magnification) and channel (e.g., color or biomarker channels). By way of example, Table 1 lists calibration values for four channels with a 40× objective and at a high numerical aperture (NA) (i.e., 0.95) for a given microscope.

TABLE 1

| Objective | Channel | Counts/Second ($I_{cal}$) | Scale (S) | Intensity Adjusted Scale Factor ($S_{cal}$) |
|---|---|---|---|---|
| 40x High NA | DAPI | 6,182.231 | 1.3 | 0.000210 |
| 40x High NA | FITC | 7,853.520 | 1.1 | 0.000140 |
| 40x High NA | CY3 | 1,684.047 | 0.9 | 0.000534 |
| 40x High NA | CY5 | 4,059.530 | 1.2 | 0.000296 |

The exposure times generated for the four channels on a given imager 12 can then be converted to $I_{exp}$ by dividing the exposure time (134) (converted to seconds) by the intensity adjusted scale factor, $S_{cal}$ (132). Table 2 depicts the respective exposure times and computed exposure counts for the example set forth in Table 1.

TABLE 2

| Objective | Channel | Exposure Counts | Exposure Time (ms) |
|---|---|---|---|
| 40x High NA | DAPI | 475.5562 | 100 |
| 40x High NA | FITC | 1,427.9130 | 200 |
| 40x High NA | CY3 | 748.4654 | 400 |
| 40x High NA | CY5 | 6,765.8830 | 2000 |

The exposure counts determined for a given imager and objective/channel combination may be used to acquire images having a standard number of counts (i.e., equivalently bright images) using different imagers 12 within a fleet of calibrated imagers. In certain embodiments, the calibration data (e.g., scale factors S, intensity adjusted scale factors $S_{cal}$, and/or exposure times, and so forth for a given calibration plate and objective channel combinations) for a given imager may be stored on the imager (such as on a memory or data storage structure accessible by the controller for the imager) such that the calibration information is always accessible to the imager. While in some embodiments, such stored calibration information may take the form of stored numeric values for one or more of these parameters. In other embodiments, the stored information may comprise one or more intermediate values from which the values may be derived or one or more images (e.g., median or average intensity images of the present calibration plate or of the master calibration plate) from which these values can be calculated as needed, i.e., on the fly. Subsequent calibrations performed on the imager may then update or overwrite the previous calibration data with more recent data. Using this calibration information, an equivalent image may be acquired using any microscope within a group of calibrated microscopes using the respective exposure count information for the objective/channel combination of interest and for the microscope used to acquire the image.

In other embodiments, the stored information may comprise one or more intermediate values from which the values may be derived or one or more images (e.g., median or average intensity images of the present calibration plate or of the master calibration plate) from which these values can be calculated as needed, i.e., on the fly. Subsequent calibrations performed on the imager may then update or overwrite the previous calibration data, whether in the form of numeric values or images, with more recent data. In one example of such an embodiment, the stored median image for a given imager 12 may be compensated by a delta median image associated with the respective calibration plate 120 that is being used in a respective calibration operation. For example, delta median images may be stored for each calibration plate 120 which allow both intensity and flattening calibrations. In one such embodiment, a stored delta median image for a calibration plate 120 may be derived by dividing the measured median image for the calibration plate 120 by the measured median image of the master calibration plate 122.

When a different imager 12 is to be used to generate an equivalent image, a respective exposure time will be calculated based on the new imagers respective exposure count information for the objective/channel of interest and an equivalent image may then be acquired using the new microscope's calibration intensity and the exposure time that yields the equivalent exposure counts. For example, turning to Table 3, intensity calibrations corresponding to those shown in Table 1 are shown for a different microscope.

TABLE 3

| Objective | Channel | Counts/Second ($I_{cal}$) | Scale (S) | Intensity Adjusted Scale Factor ($S_{cal}$) |
|---|---|---|---|---|
| 40x High NA | DAPI | 4,582.12 | 1.1 | 0.000240 |
| 40x High NA | FITC | 8,723.78 | 0.9 | 0.000103 |
| 40x High NA | CY3 | 1,365.54 | 1.1 | 0.000806 |
| 40x High NA | CY5 | 4,783.21 | 0.7 | 0.000146 |

Based on these intensity calibrations, for the second microscope the respective exposure counts along with the effective intensity adjusted scale factor can be used to determine the equivalent exposure times, as set forth in Table 4.

TABLE 4

| Objective | Channel | Exposure Counts | Exposure Time (ms) |
|---|---|---|---|
| 40x High NA | DAPI | 475.5562275 | 114.1637 |
| 40x High NA | FITC | 1,427.912642 | 147.3124 |
| 40x High NA | CY3 | 748.4653862 | 602.9204 |
| 40x High NA | CY5 | 6,765.883382 | 990.1548 |

Thus, in these example, and using the sample data provided in Tables 2 and 4, an image generated on the first microscope (Table 2) using a 40× High NA objective, the DAPI channel, and a 100 ms exposure time is equivalent in brightness to an image generated on the second microscope (Table 4) using a 40× High NA objective, the DAPI channel, and a 114.1637 ms exposure time.

Figure 11:
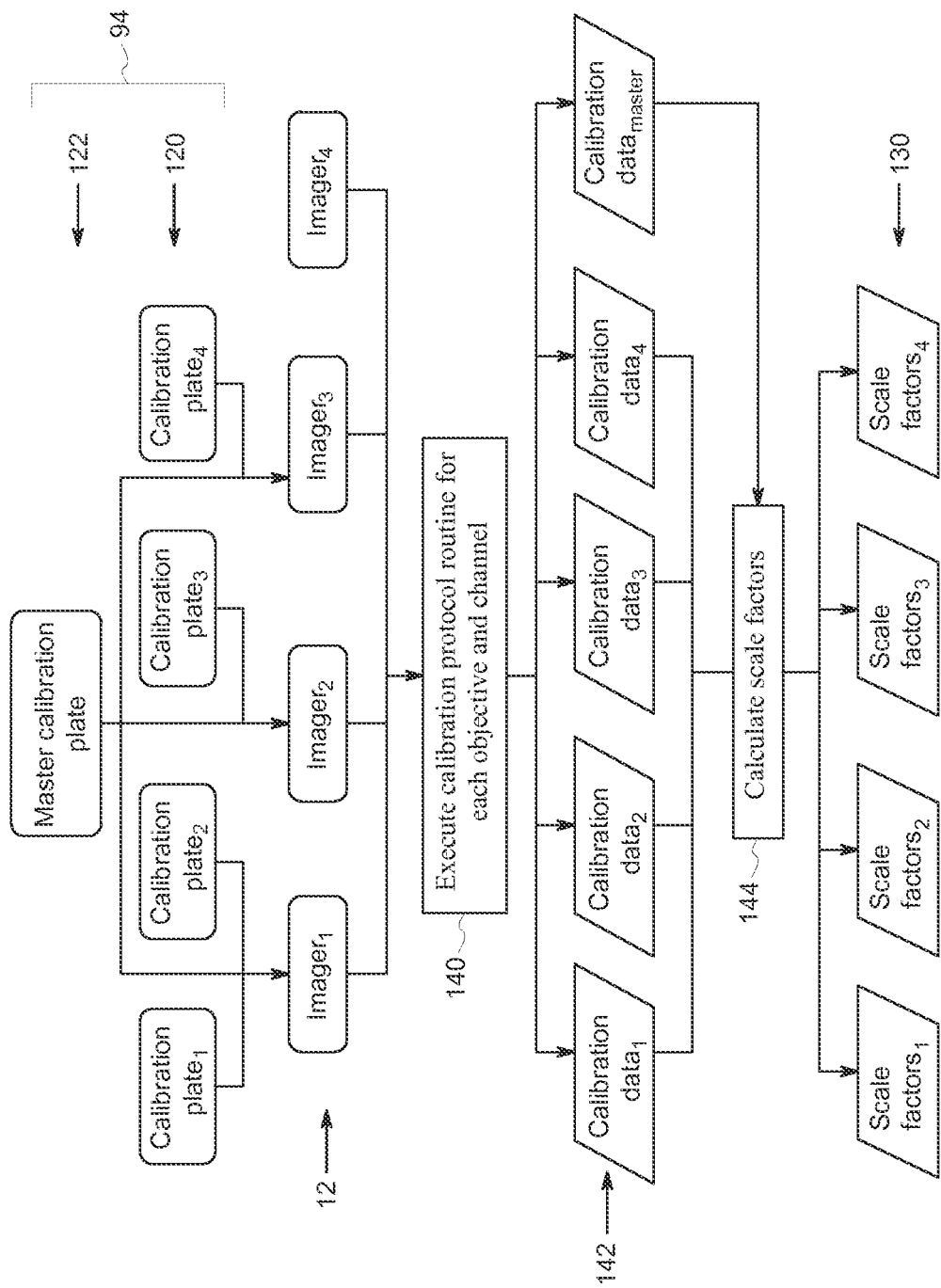
FIG. 11 depicts a process flow diagram demonstrating an inter-plate calibration, in accordance with aspects of the present disclosure.

As noted above, a single calibration plate 94 may be used to calibrate a group or fleet of imagers 12. In such implementations, the scale factor S may have a value of 1. In practice, however, where large numbers of imagers 12 are to be calibrated or where the imagers 12 are spread over multiple locations, it may be more practical to employ multiple calibration plates which are each references against a common or master calibration plate 122. By way of example, and turning to FIG. 11, in one implementation each calibration plate of a set of multiple calibration plates 94 may be assigned a unique identifier (e.g., a serial number). An inter-plate calibration may then be performed (block 140), such as by executing a processor-implemented intensity calibration script or routine, on each of the calibration plates 94 of the set to calculate a respective $I_{cal}$ for each objective and channel permutation for each calibration plate 94. In the depicted example, in some instances the same imager 12 may be used to process different calibration plates. Further, to allow calibration across the entire set of calibration plates, each non-master calibration plate 120 is calibrated with respect to the master calibration plate 122 or, at the very least, against another plate that has been calibrated against the master calibration plate 122.

The calibration results 142 may then be stored in a database or spreadsheet, a sample table 150 of which is shown as FIG. 12A (first part of the table 150) and 12B (second part of the table 150). In this example, each calibration plate is identified by a serial number 152. A field 154 also indicates which calibration plate 94 is the designated master calibration plate 122 for the group. In this example, other fields indicate the model, identification, lamp hours or age, and location of the imager 12 on which calibration was performed. Similarly, in the depicted example other fields indicate a version of the processor executable script which was run to obtain the calibration data 142, the operator who oversaw the calibration process, and the version of the holder (i.e., plate). In this example, for each calibration plate 94, an $I_{cal}$ value is stored for each objective and channel combination. The stored calibration data may serve as a traceability document for each calibration plate 94.

As discussed above, each calibration plate 94 can be categorized as a master (e.g., reference) 122 or as a holder (i.e., a non-master calibration plate 120). In the depicted example, plate "0104" is designated as a master plate 122, with the remaining plates 120 being holders. Typically only a single master 122 will be designated at one time for a given set of calibration plates 94. The intensity calibration information for the designated master plate 122 serves as the standard for the other, non-master calibration plates 120 in the set. In practice, the master calibration plate 122 may be placed in storage within a dark container after its initial intensity calibration run (or otherwise secured) to maintain the integrity of the master calibration plate 122.

Turning back to FIGS. 11 and 12A and B, in one implementation the calibration data for each non-master calibration plate 120 is compared to the calibration data for the master calibration plate 122 and a ratio (S) 130 of the given non-master plate 120 to the master plate 122 is calculated (block 144) for each objective and channel permutation. An example of such a set of ratios, based on the example of FIGS. 12A and B, is provided in Table 5:

TABLE 5

| | Non-Master:Master Ratios | | | |
| --- | --- | --- | --- | --- |
| | 0109 | 0105 | 0106 | 0111 |
| 2X_DAPI_CPS | 1.06 | 1.11 | 0.97 | 0.93 |
| 2X_FITC_CPS | 1.12 | 1.11 | 1.05 | 0.99 |
| 2X_CY3_CPS | 1.25 | 0.98 | 1.05 | 0.97 |
| 2X_CY5_CPS | 1.13 | 1.04 | 1.02 | 0.94 |
| 10X_DAPI_CPS | 1.05 | 1.09 | 1.01 | 0.95 |
| 10X_FITC_CPS | 1.15 | 1.10 | 1.11 | 1.04 |
| 10X_CY3_CPS | 1.00 | 1.01 | 1.05 | 0.98 |
| 10X_CY5_CPS | 1.13 | 1.03 | 1.05 | 0.96 |
| 20X_DAPI_CPS | 1.05 | 1.10 | 1.04 | 0.98 |
| 20X_FITC_CPS | 1.11 | 1.01 | 1.10 | 0.99 |
| 20X_CY3_CPS | 1.01 | 0.98 | 1.09 | 1.01 |
| 20X_CY5_CPS | 1.18 | 1.08 | 1.08 | 0.97 |
| 40X_DAPI_CPS | 0.93 | 0.98 | 1.12 | 0.91 |
| 40X_FITC_CPS | 0.97 | 0.85 | 1.19 | 1.07 |
| 40X_CY3_CPS | 0.89 | 0.86 | 1.07 | 1.03 |
| 40X_CY5_CPS | 1.15 | 1.10 | 1.04 | 0.97 |

These ratios, characterized as S above and herein, allows for image normalization across images (e.g., microscopes) that have been calibrated on either the same of different calibration plates 94, so long as the calibration plates employed have a known relationship to the master calibration plate 122.

Technical effects of the invention include enabling imaging across multiple imagers, such as microscopes, within a single location or across different locations. Once calibrated, microscopes may have different characteristic exposure times for different objective and channel combinations to generate images of substantially equivalent intensity, without relying on post-processing to standardize brightness. The technical effects also include the conversion of exposure times to a standard number of counts, providing a universal conversion metric that can be integrated into imaging protocols and coupled to calibration information in order to acquire normalized images.

With the preceding in mind, technical advantages include, but are not limited to: (1) by applying the calibration plate and imager-specific scale factors to determine the appropriate exposure times for acquisitions to provide substantially the same number of photons per exposure event, the signal-to-noise values of identical samples taken on different imagers will be substantially equal, and further, higher signal-to-noise values will be attained for imagers that exhibit reduced light source intensity (therefore requiring increased exposure times for equivalent image intensity) than by conventional means where intensity is normalized by post-processing the images taken with equivalent exposure times from multiple imagers; (2) by placing the calibration plate in the object plane and imaging with conventional means, the calibration results are obtained using the same physical configuration as when imaging tissue; (3) by using multiple fluorescent slides and neutral density (ND) filters on each, exposure times for optical calibrations are similar to what is used when imaging tissue, which helps to further replicate real imaging conditions to maximize accuracy of the calibrations; (4) by using laser focusing methods, repeatable intensity and illumination pattern measurements can be made on uniform fluorescent slides that have no patterned features for focusing by conventional means.

In addition, commercial advantages of the present disclosure include, but are not limited to: (1) high quality images are generated that are consistent over time, since the microscopes are periodically calibrated to a fixed calibration standard; (2) with the calibration of all microscopes to a common standard, load balancing can be performed during the multiplexing process, which improves throughput and turnaround time of the service lab; (3) by incorporating all calibration targets on a single plate and using fully automated routines, fast automated calibration can be performed, minimizing down time of the microscopes.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining a microscope exposure time, comprising:
    loading a calibration plate onto a microscope stage such that the calibration plate is positioned in the object plane of the microscope;

when the respective calibration plate is loaded, executing a calibration routine that generates a set of calibration data for each objective and channel permutation of the microscope;

calculating an intensity adjusted scale factor for at least one objective and channel permutation using the set of calibration data and a scale factor relating the respective calibration plate to a reference calibration plate or, if only a single respective calibration plate is employed, using a scale factor of 1; and using the intensity adjusted scale factors to determine an exposure time based on a photon count to be acquired at a given objective and channel combination.

2. The method of claim 1, wherein the generated set of calibration data comprises a photon count per second.

3. The method of claim 2, wherein the intensity adjusted scale factors are derived based on the respective photon count per second.

4. The method of claim 1, wherein one or more of the scale factors relating the respective calibration plate to the reference calibration plate, the intensity adjusted scale factors, or any other intensity-related numeric factors are stored on a memory of the microscope.

5. The method of claim 1, wherein one or more images from which the scale factors can be derived are stored on a memory of the microscope.

6. The method of claim 5, comprising calculating the scale factor using the one or more images as needed.

7. The method of claim 1, wherein the intensity adjusted scale factor is derived using an acquired image of a fluorescent plastic target.

8. The method of claim 7, wherein the acquired image is corrected for illumination falloff before the intensity adjusted scale factor is derived.

9. A method of performing an inter-plate calibration for a plurality of imager calibration plates, comprising:

for each calibration plate of the plurality of calibration plates, executing a calibration routine that generates a respective set of calibration data for each calibration plate, wherein each respective set of calibration data comprises measurements for each imager objective and channel permutation;

designating a master calibration plate from the plurality of calibration plates, wherein the set of calibration data for the master calibration plate is the master calibration data; and for each calibration plate, dividing the respective set of calibration data for the respective calibration plate by the master calibration data to calculate a set of scale factors for the respective calibration plate, wherein each scale factor corresponds to a different objective and channel combination.

10. The method of claim 9, wherein the set of calibration data for each calibration plate comprises a measurement of photon counts per second for each objective and channel combination used to scan the respective calibration plate.

11. The method of claim 9, comprising storing the scale factors for each calibration plate of the plurality of calibration plates or one or more images from which such scale factors may be derived for each calibration plate to allow interchangeable use of the plurality of calibration plates.

12. The method of claim 9, comprising calculating an exposure time for an imager based at least in part on the scale factors calculated for a respective calibration plate of the plurality of calibration plates.

13. The method of claim 9 wherein executing the calibration routine comprises executing an automated calibration routine on a processing component or control circuit of an imager.

14. The method of claim 9, wherein at least some of the sets of calibration data are generated on different imagers.

* * * * *